US008993004B2

(12) United States Patent
Lindner et al.

(10) Patent No.: US 8,993,004 B2
(45) Date of Patent: Mar. 31, 2015

(54) PEST CONTROL COMPOSITION

(75) Inventors: Gregory James Lindner, Wilmington, DE (US); Peter Porpiglia, Putnam Valley, NY (US)

(73) Assignee: Croda, Inc., Edison, NJ (US)

( * ) Notice: Subject to any disclaimer, the term of this patent is extended or adjusted under 35 U.S.C. 154(b) by 425 days.

(21) Appl. No.: 12/662,164

(22) Filed: Apr. 1, 2010

(65) Prior Publication Data

US 2010/0260873 A1 Oct. 14, 2010

Related U.S. Application Data

(60) Provisional application No. 61/202,780, filed on Apr. 3, 2009.

(51) Int. Cl.
| | |
|---|---|
| *A61K 36/00* | (2006.01) |
| *A61K 36/53* | (2006.01) |
| *A01N 25/30* | (2006.01) |
| *A01N 25/04* | (2006.01) |
| *A01N 37/06* | (2006.01) |
| *A01N 65/00* | (2009.01) |
| *A01N 65/16* | (2009.01) |
| *A01N 65/22* | (2009.01) |

(52) U.S. Cl.
CPC .............. *A01N 25/30* (2013.01); *A01N 25/04* (2013.01); *A01N 37/06* (2013.01); *A01N 65/00* (2013.01); *A01N 65/16* (2013.01); *A01N 65/22* (2013.01)
USPC ........................................................ 424/725

(58) Field of Classification Search
None
See application file for complete search history.

(56) References Cited

U.S. PATENT DOCUMENTS

| 1,937,969 | A | * | 12/1933 | Knight | 424/731 |
| 4,707,496 | A | * | 11/1987 | Simmons | 514/531 |
| 4,861,762 | A | * | 8/1989 | Puritch et al. | 514/122 |
| 5,240,708 | A | | 8/1993 | Plummer et al. | |
| 5,631,290 | A | * | 5/1997 | Almond et al. | 514/560 |
| 5,792,465 | A | * | 8/1998 | Hagarty | 424/405 |
| 2006/0165748 | A1 | * | 7/2006 | Arimoto | 424/405 |
| 2006/0204468 | A1 | * | 9/2006 | Allef et al. | 424/70.13 |
| 2008/0020078 | A1 | * | 1/2008 | Enan | 424/776 |
| 2010/0303940 | A1 | * | 12/2010 | Enan | 424/778 |

FOREIGN PATENT DOCUMENTS

| EP | 0617888 | 10/1994 |
| WO | WO 01/91555 | 12/2001 |

OTHER PUBLICATIONS castor oil from Wikipedia, access on May 25, 2011, pp. 1-10.*
International Search Report dated Mar. 18, 2011 for PCT/US2010/029637.
Akpan et al., "Fatty Acid Profile and Oil Yield in Six Different Varieties of Fresh and Dry Samples of Coconuts (*Cocos nucifera*)", Pakistan Journal of Nutrition, vol. 5, No. 2, 2006, pp. 106-109.
Kabara, "Fatty acids and Esters as Antimicrobial/Insecticidal Agents", American Chemical Society, 1987, pp. 220-238.
Baldwin et al., "Toxicity of Fatty Acids to German and American Cockroaches", Entomological Society of America, vol. 101, No. 4, Aug. 2008, pp. 1384-1388.

* cited by examiner

*Primary Examiner* — Qiuwen Mi
(74) *Attorney, Agent, or Firm* — Jones Day

(57) ABSTRACT

A composition contains at least one pest control active and a mixture of unsaturated C12-C26 fatty acids and/or salts thereof and saturated C6-C14 fatty acids and/or salts thereof. The pest control active is preferably at least one plant essential oil. The composition is suitably in the form of an emulsion, particularly a transparent microemulsion. The mixture of fatty acids and/or salts thereof can be used as part of, or as the sole, emulsifying system. The emulsion can exhibit improved pest control properties.

24 Claims, No Drawings

PEST CONTROL COMPOSITION

CROSS REFERENCE TO RELATED APPLICATION

This application claims the benefit of priority from U.S. Provisional Application No. 61/202,780, filed Apr. 3, 2009. This related application, in its entirety, is hereby incorporated by reference.

FIELD OF INVENTION

The present invention relates to a composition comprising a pest control active and a mixture of fatty acids and/or salts thereof, in particular such a composition in the form of an emulsion, and methods of making thereof.

BACKGROUND OF THE INVENTION

Although humans have used chemicals to control pests since before 2500 BC, it is only relatively recently that chemical control has been widely used. Early pesticides included hellebore to control body lice, nicotine to control aphids, and pyrethrum to control insects. In 1939 DDT was discovered to be a very effective insecticide and quickly became the most widely used pesticide in the world. In the 1940's manufacturers began to produce large amounts of synthetic pesticides and their use became widespread. Further developments of pesticides followed, and with their relatively low cost, ease of use and effectiveness, they became the primary means of pest control.

Although there are many benefits to the use of pest control materials and pesticides, there are also drawbacks, such as potential toxicity to humans and other animals, as well as persistence and accumulation of toxic materials in the environment. There is a growing requirement for more natural pest control actives that are safer, do not persist in, and are friendlier to the environment. There is also a need for improved formulation such that the odour and/or stability of the composition is improved, more consistent pest control is obtained, and/or the effectiveness of pest control is increased. This can enable lower concentrations of actives to be used, with a resultant reduced detrimental impact on the environment.

SUMMARY OF THE INVENTION

We have now surprisingly discovered a composition and emulsion that overcomes or significantly reduces at least one of the aforementioned problems.

Accordingly, the present invention provides a composition comprising at least one pest control active and a mixture of unsaturated C12-C26 fatty acids and/or salts thereof and saturated C6-C14 fatty acids and/or salts thereof.

The invention also provides an emulsion comprising;
  i) an oil phase,
  ii) at least one pest control active,
  iii) a mixture of unsaturated C12-C26 fatty acids and/or salts thereof and saturated C6-C14 fatty acids and/or salts thereof,
  iv) an optional organic cosolvent, and
  v) water.

The invention further provides a method of forming an end-use pest control product comprising forming an emulsion which comprises;
  i) 3 to 50% by weight of an oil phase,
  ii) 0.5 to 40% by weight of at least one pest control active,
  iii) 3 to 50% by weight of a mixture of unsaturated C12-C26 fatty acids and/or salts thereof and saturated C6-C14 fatty acids and/or salts thereof,
  iv) 0 to 20% by weight of an organic cosolvent, and
  v) the balance water,
  vi) and diluting said emulsion with water up to 15 times.

The invention yet further provides a composition comprising, consisting essentially of, or consisting of, fatty acids and/or salts thereof comprising, consisting essentially of, or consisting of, a mixture of unsaturated C12-C26 fatty acids and/or salts thereof and saturated C6-C14 fatty acids and/or salts thereof.

The invention still further provides the use of a mixture of unsaturated C12-C26 fatty acids and/or salts thereof and saturated C6-C14 fatty acids and/or salts thereof as an emulsifier system to form an emulsion.

Pests may include any form of life such as insects; weeds; mollusks; birds; mammals, particularly rodents; fish; fungi and microbes that compete with humans for food, destroy property, spread and/or are a vector for disease or cause a nuisance. The composition according to the present invention is particularly suitable for treating "insects", which term is used herein for the purpose of simplicity to cover arthropods in general, i.e. not only true insects, but also, for example, arachnids, larvae, mites and other invertebrates.

In one embodiment, the pest is selected from the group consisting of German cockroach, harvester ant, darkling beetle, mealworm (larval darkling beetle), American cockroach, Argentine ant, big-headed ant, bed bug, cat flea, crazy ant, diamondback moth, Eastern subterranean termite, flour beetle, ghost ant, honey bee, house cricket, house fly, house spider, millipede, pharaoh ant, red imported fire ant, yellow fever mosquito, lesser grain borer, and brown dog tick.

The term "pest control" as used herein means the presence of a repellent effect, a pesticidal effect, or both, that is attributable to the presence of an active ingredient.

The term "repellent effect" is an effect, wherein more pests, preferably insects, are repelled away from a host or area that has been treated with a pest control composition than a control or host area that has not been so treated. In one embodiment, repellent effect is an effect wherein at least 40%, preferably at least 60%, more preferably at least 75%, and particularly at least 90% of pests are repelled away from a host or area that has been treated with the composition.

The term "pesticidal effect" is an effect, wherein treatment with a pest control composition causes at least 1% of the pests, preferably insects, to die. In one embodiment, the pesticidal effect is an effect wherein treatment with a composition causes at least 5%, suitably at least 10%, preferably at least 25%, more preferably at least 50%, particularly at least 75%, and especially at least 90% and up to 100% of the exposed pests to die. For insect control, in one embodiment of the invention, treatment with a pest control composition will result in knockdown of the insects occurring within a few, e.g. 5 to 20, seconds to a few, e.g. 2 to 5, minutes.

The composition of the present invention suitably exhibits improved, preferably synergistic, pest control effect, for example having (i) preferably greater than 10%, more preferably greater than 30%, particularly greater than 50%, and especially greater than 70% repellent effect; (ii) preferably greater than 10%, more preferably greater than 30%, particularly greater than 50%, and especially greater than 70% pesticidal effect, and/or (iii) preferably greater than 20%, more preferably greater than 40%, particularly greater than 60%, and especially greater than 80% increased speed of repellent and/or pesticidal effect (e.g. when measured after 100 seconds for treatment of German cockroaches); all compared to a control composition formulated with the same pest control active at the same concentration, but without the mixture of the unsaturated and saturated fatty acids and salts thereof described herein. A suitable control contains 1% tetraglycerol oleate, 1% lecithin, and 2.1% xanthan gum, instead of the fatty acids and/or salts thereof mixture described herein.

The compositions of the present invention may be used to control pests by either treating the pest directly, a host directly, or treating an area in which the host will be located, for example, an indoor living space, outdoor patio or garden. The host may be a plant, human or other animal.

The pest control active may be any known repellent, pesticide, insecticide, acaricide, miticide, nematicide, fungicide, bactericide, rodenticide, virucide, and/or herbicide. In one embodiment the pest control active is an insect repellent or insecticide, including an ovicide, larvicide and adulticide. The insect control active may, for example, be DEET, D-allethrin, lambda-cyhalothrin, and/or terpenoid containing natural oil or plant essential oil.

The amount of pest control active present in a composition according to the present invention is suitably in the range from 0.5 to 40%, preferably 1 to 20%, more preferably 2 to 15%, particularly 3 to 5%, and especially 5 to 10% by weight, based on the total weight of the composition. Alternatively, the amount of pest control active can be expressed in relation to the concentration of the fatty acids and/or salts thereof, and therefore is preferably present at a concentration in the range from 15 to 200%, more preferably 20 to 100%, particularly 25 to 70%, and especially 30 to 50% by weight, based on the weight of the fatty acids and/or salts thereof in the composition.

In a preferred embodiment of the present invention, the pest control active is at least one terpenoid containing natural oil or plant essential oil. Suitable oils include materials selected from the group consisting of t-anthole, lime oil, piperonyl, black seed oil (BSO), d-limonene, piperonyl acetate, camphene, linalyl anthranilate, piperonyl alcohol, carvacrol, linalool, piperonyl amine, d-carvone, lindenol, quinine, 1-carvone, methyl citrate, sabinene, 1,8-cineole, alpha-terpinene, p-cymene, hydrojasmonate, terpinene 900, diethyl phthalate, myrcene, alpha-terpineol, eugenol, perillyl alcohol, gamma-terpineol, geraniol, phenyl acetaldehyde, 2-tert-butyl-p-quinone, alpha-pinene, alpha-thujone, lemon grass oil, beta-pinene, thyme oil, lilac flower oil (LFO), piperonal, thymol, wintergreen oil, and mixtures thereof. Preferred materials are selected from the group consisting of thyme oil, geraniol, wintergreen oil, lemon grass oil, lilac flower oil, black seed oil, lime oil, eugenol, and mixtures thereof. Particularly preferred materials are selected from the group consisting of thyme oil, geraniol, wintergreen oil, and mixtures thereof.

In one embodiment, mixtures of 2 or more terpenoid containing natural oils or plant essential oils are used. The use of such mixtures can result in synergistic pest control effects. Preferred mixtures include two or more selected from the group consisting of thyme oil, geraniol, and wintergreen oil.

Preferred pest control active thyme oil is a natural product that can be extracted from certain plants, including species from the Labiatae family; for example, thyme oil can be obtained from *Thymus vulgaris* (also known as, *T. ilerdensis, T aestivus*, and *T. velantianus*). Thyme oil red is an unrefined extract, while the refined extract is often termed thyme oil white.

Preferred pest control active geraniol, also called rhodinol, is a monoterpenoid and an alcohol. It is the primary part of oil-of-rose and palmarosa oil. It is used in perfumes and as a flavoring. It is also produced by the scent glands of honey bees to help them mark nectar-bearing flowers and locate the entrances to their hives.

Preferred pest control active wintergreen oil is from the shrub genus *Gaultheria*. Methyl salicylate, the main constituent of the oil, is not present in the plant until formed by enzymatic action from a glycoside within the leaves.

The unsaturated and saturated fatty acids used in the present invention are in the form of the free fatty acid and/or salt thereof. Suitable salts are alkali metal salts, such as sodium, and/or potassium; ammonium salts; and/or alkylamine salts, such as isopropylamine, aminomethylpropanol, monoethanolamine, diethanolamine, and/or triethanolamine. Alkali metal, particularly potassium, salts are preferred.

The fatty acid salts are preferably formed in situ by the addition of suitable salt forming material, e.g. base, such as sodium hydroxide, preferably potassium hydroxide, to the fatty acid containing composition. The base is preferably added as a relatively dilute aqueous solution, e.g. at a concentration of 1 to 30%, preferably 5 to 20%, more preferably about 10 to 15% w/w. The addition of base can be used to control the pH of the composition which is preferably in the range from 6 to 9, more preferably 7 to 8.5, particularly 7.2 to 8.2, and especially 7.5 to 8. A surprising improvement in the pest control properties of the composition can be achieved at these pH values.

In one embodiment, the amount of fatty acid salts in the composition is preferably in the range from 50 to 100%, more preferably 90 to 99.9%, particularly 95 to 99.5%, and especially 96 to 99% by weight, based on the total weight of fatty acids and salts thereof in the composition. Correspondingly, the amount of free fatty acids is preferably in the range from 0 to 50%, more preferably 0.1 to 10%, particularly 0.5 to 5%, and especially 1 to 4% by weight, based on the total weight of fatty acids and salts thereof in the composition.

The unsaturated fatty acids and/or salts thereof used in the present invention comprise, consist essentially of, or consist of, in the range from 12 to 26, preferably 14 to 24, more preferably 16 to 22, particularly 18 to 20, and especially 18 carbon atoms. In one embodiment, greater than 50%, preferably greater than 60%, more preferably greater than 70%, particularly greater than 80%, and especially greater than 90% and up to 100% by weight of the unsaturated fatty acids fall within one or more of the above carbon atom ranges, based on the total weight of unsaturated fatty acids in the composition.

Suitable unsaturated fatty acids are selected from the group consisting of oleic, elaidic, ricinoleic, dodecenoic, tetradecenoic (myristoleic), hexadecenoic (palmitoleic), octadecadienoic (linoleic or linolelaidic), octadecatrienoic (linolenic), eicosenoic (gadoleic), eicosatetraenoic (arachidonic), docosenoic (erucic), docosenoic (brassidic), docosapentaenoic (clupanodonic), eicosapentaenoic, docosahexaenoic, gamma-linolenic, dihomo-gamma-linolenic, arachidonic, acids, and mixtures thereof. Preferred unsaturated fatty acids are selected from the group consisting of oleic, ricinoleic, linoleic, linolenic, acids and mixtures thereof. Particularly preferred unsaturated fatty acids are selected from the group consisting of oleic, ricinoleic, linoleic, acids and mixtures thereof.

The unsaturated fatty acids are preferably monocarboxylic acids and may be linear or branched, and are preferably linear. The unsaturated fatty acids may be in the form of cis and/or trans isomers. Oleic acid is a preferred cis isomer, and elaidic acid a preferred trans isomer. The unsaturated fatty acids may be unsubstituted, or substituted, for example with one or more hydroxyl groups. Ricinoleic acid is a preferred hydroxy acid.

The unsaturated fatty acids may be mono-unsaturated, di-unsaturated or polyunsaturated, i.e. containing one, two or more than two carbon-carbon double bonds respectively. Oleic acid is a preferred mono-unsaturated fatty acid, and linoleic acid is a preferred di-unsaturated fatty acid. In one embodiment, the concentration of (i) mono-unsaturated fatty acids is preferably greater than 10%, more preferably greater than 20%, and particularly in the range from 30 to 90%, by weight, (ii) di-unsaturated fatty acids is preferably greater than 5%, more preferably greater than 10%, and particularly in the range from 15 to 50% by weight, (iii) mono-unsaturated and di-unsaturated fatty acids combined is preferably greater than 75%, more preferably greater than 85%, particularly greater than 90%, and especially in the range from 95 to 100% by weight, and/or (iv) polyunsaturated fatty acids is preferably less than 25%, more preferably less than 15%, particularly less than 5%, and especially in the range from 0 to 3% by weight, all based on the total weight of unsaturated fatty acids in the composition.

The concentration of unsaturated fatty acids and/or salts thereof present in a composition according to the present invention is suitably in the range from 10 to 90%, preferably 20 to 80%, more preferably 30 to 70%, particularly 40 to 60%, and especially 45 to 55% by weight, based on the total weight of fatty acids and salts thereof in the composition.

In one embodiment of the present invention, the unsaturated fatty acids and/or salts thereof comprise a mixture of unsubstituted fatty acids and hydroxy fatty acids, preferably present at a ratio of 10 to 90%:10 to 90%, more preferably 30 to 70%:30 to 70%, particularly 40 to 60%:40 to 60%, and especially 45 to 55%:45 to 55% by weight, based on the total weight of unsaturated fatty acids and salts thereof in the composition. A particularly preferred combination is a mixture of oleic acid and ricinoleic acid.

The saturated fatty acids and/or salts thereof used in the present invention comprise, consist essentially of, or consist of, in the range from 6 to 14, preferably 6 to 12, more preferably 8 to 12, and particularly 8 to 10 carbon atoms. In one embodiment, greater than 50%, preferably greater than 60%, more preferably greater than 70%, particularly greater than 80%, and especially greater than 90% and up to 100% by weight of the saturated fatty acids and/or salts thereof fall within one or more of the above carbon atom ranges, based on the total weight of saturated fatty acids and salts thereof in the composition.

The saturated fatty acids are preferably monocarboxylic acids and may be linear and/or branched, and are preferably linear.

Suitable saturated fatty acids are selected from the group consisting of hexanoic (caproic), octanoic (caprylic), nonanoic, decanoic (capric), undecanoic, dodecanoic (lauric), tridecanoic, tetradecanoic acid (myristic), 2-ethyl hexanoic, trimethylhexanoic, trimethylnonanoic, acids and mixtures thereof. Preferred saturated fatty acids are selected from the group consisting of caprylic, capric, 2-ethyl hexanoic, trimethylhexanoic, trimethylnonanoic, tetramethylhexanoic, acids, and mixtures thereof. Particularly preferred saturated fatty acids are selected from the group consisting of caprylic, capric, 2-ethyl hexanoic, trimethylhexanoic, acids, and mixtures thereof.

The concentration of saturated fatty acids and/or salts thereof present in a composition according to the present invention is suitably in the range from 10 to 90%, preferably 20 to 80%, more preferably 30 to 70%, particularly 40 to 60%, and especially 45 to 55% by weight, based on the total weight of fatty acids and salts thereof in the composition.

The ratio by weight of unsaturated fatty acids and/or salts thereof to saturated fatty acids and/or salts thereof in a composition according to the present invention is preferably in the range from 0.2 to 5:1, more preferably 0.35 to 3:1, particularly 0.5 to 2:1, and especially 0.8 to 1.2:1.

In one embodiment, the mean number of carbon atoms, on a weight basis, present in the unsaturated fatty acids and/or salts thereof is suitably at least 2, preferably at least 4, more preferably in the range from 6 to 12, particularly 7 to 11, and especially 8 to 10 carbon atoms greater than the mean number of carbon atoms present in the saturated fatty acids and/or salts thereof. The mean number of carbon atoms by weight present in the unsaturated fatty acids and/or salts thereof is preferably in the range from 14 to 22, more preferably 16 to 20, particularly 17 to 19, and especially 17.5 to 18.5. The mean number of carbon atoms by weight present in the saturated fatty acids and/or salts thereof is preferably in the range from 6 to 12, more preferably 7 to 11, particularly 8 to 10, and especially 8.5 to 9.5.

The fatty acids and/or salts thereof are suitably present in a composition according to the present invention in the range from 3 to 50%, preferably 5 to 40%, more preferably 10 to 30%, particularly 15 to 25%, and especially 18 to 22% by weight, based on the total weight of the composition. Alternatively, the amount of fatty acids and/or salts thereof can be expressed in relation to the concentration of the pest control active and therefore are preferably present at a concentration in the range from 50 to 500%, more preferably 100 to 400%, particularly 150 to 350%, and especially 200 to 300% by weight, based on the weight of the pest control active.

In one preferred embodiment of a composition according to the present invention, the concentration of (i) unsaturated fatty acids and/or salts thereof to saturated fatty acids and/or salts is preferably in the range from 10 to 45%:55 to 90%, more preferably 15 to 40%:60 to 85%, particularly 20 to 35%:65 to 80%, and especially 25 to 30%:70 to 75% by weight, based on the total weight of fatty acids and salts thereof in the composition, and/or (ii) total fatty acids and/or salts thereof is preferably in the range from 5 to 20%, more preferably 7 to 17%, particularly 9 to 15%, and especially 10 to 14% by weight, based on the total weight of the composition.

Fatty acids suitable for use herein, can be obtained from natural sources such as, for example, plant or animal esters (e.g. palm oil, rape seed oil, palm kernel oil, coconut oil, babassu oil, soybean oil, castor oil, tallow, whale or fish oils, grease, lard, and mixtures thereof). Fatty acids derived from plant sources are preferred. Normally purified or distilled unsaturated and/or saturated fatty acids will be employed, but naturally occurring mixtures may also be used where appropriate, e.g. when high in unsaturated fatty acids such as soybean, linseed, sunflower, corn, onagra, and/or borage, oil fatty acids. The fatty acids may also be synthetically prepared, for example as described in "Fatty Acids in Industry", Ed Robert W Johnson, Earl Fritz, Marcel Dekker Inc, 1989 ISBN 0-8247-7672-0.

The composition may also comprise at least one organic carrier oil or emollient such as a mineral oil, food oil, or vegetable oil, e.g. fatty acid glyceride, fatty acid ester and fatty alcohol. Examples of suitable relatively non-polar oils include C13-C14 isoparaffin, isohexadecane, paraffinum liquidum (mineral oil), squalane, squalene, hydrogenated polyisobutene, and polydecene; and relatively polar materials include C12-C15 alkyl benzoate, caprylic/capric triglyceride, cetearyl isononanoate, ethylhexyl isostearate, ethylhexyl palmitate, isononyl isononanoate, isopropyl isostearate, isopropyl myristate, isostearyl isostearate, isostearyl neopentanoate, octyldodecanol, pentaerythrityl tetraisostearate, PPG-15 stearyl ether, triethylhexyl triglyceride, dicaprylyl carbonate, ethylhexyl stearate, *helianthus annus* (sunflower) seed oil, isopropyl palmitate, and octyldodecyl neopentanoate. Isopropyl myristate is a preferred carrier material.

The concentration of the carrier material may vary widely. The amount of the carrier material is suitably in the range from 0.5 to 40%, preferably 1 to 20%, more preferably 2 to 15%, particularly 3 to 10%, and especially 4 to 8% by weight, based on the total weight of the composition.

The composition may be in any suitable form, but preferably is an emulsion (or suspoemulsion), such as a water-in-oil or oil-in-water, preferably an oil-in-water emulsion. The mixture of fatty acids and/or salts thereof described herein are suitable for use in forming emulsions, i.e. as the, or as part of the, emulsifier system. The emulsifier system comprises, consists essentially of, or consists of, a mixture of unsaturated and saturated fatty acids and/or salts thereof as described herein. A particularly surprising feature of the present invention is that emulsions can be produced using the fatty acid mixture as the sole component of the emulsifier system, i.e. effectively in the absence of any other surfactant or emulsifier components. By "effective absence" is meant preferably less than 10%, more preferably less than 5%, and particularly less than 2% by weight of any additional anionic, cationic, amphoteric, zwitterionic and/or non-ionic, particularly alkoxylated, surfactants or emulsifiers, based on the total weight of fatty acids and/or salts thereof in the emulsion.

The emulsion may for example be a microemulsion or nanoemulsion, preferably a microemulsion. The emulsion may be bicontinuous or have a mean droplet size over a wide range, preferably in the range from 1 to 1,000 nm, more preferably 5 to 500 nm, and particularly 10 to 100 nm. The emulsion droplet size may be reduced by suitable means, for example by high pressure homogenization.

The oil phase of the emulsion may comprise at least one of the carrier oils or emollients described herein and/or at least one pest control active, preferably one or more terpenoid containing natural oils or plant essential oils as described herein.

The ratio by weight of carrier material to pest control active in the oil phase is preferably in the range from 0.1 to 5:1, more preferably 0.3 to 3:1, particularly 0.4 to 2:1, and especially 0.5 to 1:1.

In one embodiment, the oil phase comprises, consists essentially of, or consists of, a blend of isopropyl myristate, geraniol and/or thyme oil white, suitably at a concentration of 30 to 45% by weight isopropyl myristate, 20 to 40% by weight geraniol and/or 25 to 40% by weight thyme oil white, based on the total weight of the oil phase.

In another embodiment, the oil phase comprises, consists essentially of, or consists of, a blend of isopropyl myristate, wintergreen oil and/or thyme oil white and thyme oil red, suitably at a concentration of 30 to 40% by weight isopropyl myristate, 40 to 50% by weight wintergreen oil and/or 15 to 25% by weight of a 99:1 mixture of thyme oil white and thyme oil red, based on the total weight of the oil phase.

The concentration of the oil phase may vary widely. The amount of the oil phase in the emulsion is suitably in the range from 1 to 90%, preferably 3 to 50%, more preferably 5 to 30%, particularly 8 to 20%, and especially 10 to 15% by weight, based on the total weight of the emulsion.

The fatty acids and/or salts thereof are preferably present in an emulsion according to the present invention in the range from 50 to 300%, more preferably 75 to 250%, particularly 100% to 200%, and especially 100 to 150% by weight, based on the total weight of the oil phase.

The amount of water present in the emulsion is suitably in the range from 10 to 95%, preferably 20 to 85%, more preferably 30 to 80%, particularly 40 to 75%, and especially 50 to 70% by weight, based on the total weight of the emulsion.

The emulsion may also comprise an additional organic cosolvent preferably present at a concentration in the range from 0 to 100%, more preferably 5 to 90%, particularly 20 to 80%, and especially 30 to 50% by weight, based on the total weight of fatty acids and/or salts thereof in the emulsion.

The cosolvent is suitably relatively polar, and preferably is a lower alcohol or ester having a molecular weight of less than 400, more preferably less than 200, and particularly in the range from 40 to 100. Isopropanol and/or ethanol are particularly preferred lower alcohol cosolvents.

The emulsion according to the present invention preferably exhibits stability against emulsion separation, i.e. the emulsion remains homogeneous when stored for extended periods at various temperatures. The emulsion is preferably stable, measured as herein described, at 5° C., more preferably at 25° C., particularly at 40° C., and especially at 50° C., preferably for at least one month, more preferably at least 2 months, and particularly for at least 3 months. The stability at elevated temperatures, i.e. at 40° C. and 50° C., is a particularly important property and can be difficult to achieve.

The emulsion is suitably transparent. By "transparent" is meant having the property of transmitting light without appreciable scattering, so that objects, for example written text, e.g. this patent specification, placed behind the emulsion are entirely visible and can easily be discerned or in the case of written text, read. The amount of light transmitted is, of course, dependent upon the thickness of the emulsion, and in the present context the emulsion can be placed in a clear glass cuvette of 20 mm thickness.

One advantage of the present invention is that emulsions can be produced comprising only ingredients that are described in numerous lists of permissible or exempt ingredients maintained by the US Federal government. Compositions containing only such ingredients face much lower regulatory barriers and consequently are much easier to introduce into the marketplace. These lists include, for example, those set forth in Environmental Protection Agency regulations, such as 40 C.F.R. §180.950, as well as those described in the Federal Insecticide, Fungicide and Rodenticide Act (FIFRA)'s §25(b) and 4(a) Food-Use Non-Food Use listings for pesticide products.

The emulsions of the invention may be made by generally conventional emulsification and mixing methods. For example, the unsaturated and saturated fatty acids may be added to (i) the oil phase, to which is then added the aqueous phase, (ii) both the combined oil and aqueous phases, (iii) the aqueous phase, to which is then added the oil phase, or (iv) the saturated fatty acids are added to the aqueous phase and the unsaturated fatty acids are added to the oil phase, the two phases being subsequently combined. Method (i) is preferred. The salt forming moiety or base is suitably incorporated in the aqueous phase prior to mixing with the oil phase. Since the combination of the base with the fatty acids is exothermic, heating is generally not required to form the emulsion. In all of these methods, the resulting mixture can form a stable emulsion, particularly when the base is introduced as part of the aqueous phase. Sufficient base can be added to obtain the required pH. The preferred embodiment forms a stable transparent microemulsion. The emulsion can be formed in one process vessel, through a single contiguous series of steps.

The emulsions are preferably formed at low or ambient temperature and/or at low to moderate shear. Low temperature or cold processing is particularly advantageous where volatile oils are being used which could be lost or degraded at high temperatures, or which may be subject to increased risk of fire or explosion. It is a feature of the present invention that stable emulsions can be produced at low temperature, and with suitable low viscosity at these temperatures, to allow low shear mixing.

By the term "low temperature" is meant a temperature of not more than 60° C., preferably not more than 50° C. and especially not more than 40° C. Additionally, the term "low temperature" means a temperature of greater than 0° C., preferably at least 10° C., and especially at least 15° C. Preferred temperatures are in the range from 15° C. to 50° C., more preferably 20° C. to 40° C.

By the term "low shear" is meant a shear rate of not more than 5000 s$^{-1}$. Additionally, the term "low shear" means a shear rate of greater than 10 s$^{-1}$, preferably at least 50 s$^{-1}$.

The emulsions can also be made by inverse emulsification methods, whereby the fatty acid mixture is added to the oil phase, the aqueous phase is then added and mixed into the oil phase to form a water-in-oil emulsion. Aqueous phase addition, including base, is continued until the system inverts to form an oil-in-water emulsion. Plainly a substantial amount of aqueous phase and/or the inclusion of sufficient base to achieve a final pH of at least 7 will generally be needed to effect complete inversion and so this method is not likely to be used for very high oil phase content emulsions.

The emulsions described herein may be used directly to control pests, or the emulsion may be used as a pre-concentrate enabling dilution with water, for example up to 15 times, preferably up to 10 times, particularly in the range from 1 to 7, and especially 3 to 5 times. A feature of the present invention is that stable, transparent emulsions can be obtained after such a dilution, giving increased flexibility to the end-use formulator.

The emulsion described herein is particularly suitable for use as a sprayable product. Such emulsions suitably have a low shear viscosity of up to 2000, preferably up to 1000, more preferably in the range from 1 to 500, particularly 1 to 300, and especially 1 to 100 mPa·s. The most preferred microemulsion formulations generally display Newtonian (non-shear thinning) behavior although bicontinuous microemulsion systems are shear-thinning.

In this specification the following test methods have been used:
(i) Viscosity was measured with a Brookfield DV II+ viscometer using an appropriate spindle (LV1, LV2, LV3, or LV4—depending on the viscosity of the emulsion being tested) at 6 rpm (0.1 Hz), 1 day after making the emulsions and results are quoted in mPa·s.
(ii) Stability was assessed by observing the emulsions after storage at ambient temperature (20 to 25° C.), cold at 5° C. or under elevated temperature storage at 40° C. and 50° C. The composition is stable if the emulsion remains transparent and no visible separation of the emulsion occurs.

The invention is illustrated by the following non-limiting examples.

EXAMPLES

Example 1

An emulsion was made at ambient temperature, by adding 40 g of a 50:50% by weight fatty acid mixture of oleic acid and capric acid/caprylic acid (50:50% by weight) to 20 g isopropanol, and 30 g of an essential oil mixture containing 38.5% by weight isopropyl myristate, 31.6% by weight thyme oil white, and 29.9% by weight geraniol, in a 250 ml glass beaker, under constant agitation (magnetic stirrer, 200-300 rpm). 60 g of 15% by weight aqueous potassium hydroxide solution was then added to the beaker. The mixer was operated until the emulsion appeared to be homogenous and clear (approximately 10 minutes). The pH was measured and confirmed to be between 7.8 and 8.2. 50 g of water was added and the pH remeasured after allowing the electrode to equilibrate for 10 to 30 minutes. The pH was again between 7.8 and 8.2.

Example 2

The procedure of Example 1 was repeated except that the essential oil mixture contained 34.3% by weight isopropyl myristate, 20.6% by weight of a 99:1 mixture of thyme oil white and thyme oil red, and 45.1% by weight wintergreen oil.

Example 3

The procedure of Example 1 was repeated except that soya fatty acids were used instead of oleic acid.

Example 4

The procedure of Example 1 was repeated except that 2-ethyl hexanoic acid was used instead of capric acid/caprylic acid.

Example 5

The procedure of Example 1 was repeated except that trimethyl hexanoic acid was used instead of capric acid/caprylic acid.

Example 6

The procedure of Example 1 was repeated except that half of the oleic acid was replaced with ricinoleic acid.

Example 7

The procedure of Example 1 was repeated except that ricinoleic acid was used instead of oleic acid.

Example 8

The procedure of Example 1 was repeated except that 36 g of a 28:72% by weight fatty acid mixture of the oleic acid and capric acid/caprylic acid, 7.5 g isopropanol, 15 g of the essential oil mixture, and 3 g of butyl lactate were used. 132 g of 7.5% by weight aqueous potassium hydroxide solution was used to adjust the pH to be between 8.0 and 8.3. 106 g of water was added, and the pH after mixing was again between 8.0 and 8.3.

All of the emulsions made in Examples 1 to 8 had viscosities of less than 100 mPa·s at temperatures ranging from 25 to 50° C., and remained stable (clear microemulsions) overnight at laboratory temperature (20-25° C.) and at 50° C.

Example 9

The emulsions produced in Examples 1 and 8 were sprayed onto German cockroaches, and knockdown data obtained over time (20 to 3600 seconds). The results were compared with control samples; (i) containing 1% tetraglycerol oleate, 1% lecithin, and 2.1% xanthan gum, and the balance water, instead of the fatty acid mixture, and (ii) containing mineral oil instead of the essential oil mixture. The emulsions of both Examples 1 and 8 exhibited much faster knockdown effects than the controls.

Example 10

The emulsion produced in Example 2 was sprayed onto harvester ants and knockdown data obtained over time. The results were compared with those obtained using the tetraglycerol oleate/lecithin/xanthan gum control described in Example 9, and the efficacy was approximately double the control.

The above examples illustrate the improved properties of a composition and emulsion according to the present invention.

What is claimed is:

1. An emulsion composition, comprising:
   i) at least one pest control active; and
   ii) a mixture of:
      a) unsaturated C12-C26 fatty acids and/or salts thereof; and
      b) saturated C6-C14 fatty acids and/or salts thereof, wherein greater than 70% by weight of the saturated fatty acids comprise 6 to 12 carbon atoms;
   wherein the ratio of the unsaturated fatty acid component to the saturated fatty acid component in the composition is in the range from 0.2 to 5:1 by weight.

2. The emulsion composition according to claim 1 comprising 0.5 to 40% by weight of pest control active.

3. The emulsion composition according to claim 1 wherein the pest control active is thyme oil, geraniol, and/or wintergreen oil.

4. The emulsion composition according to claim 1 comprising 3 to 50% by weight of the mixture of unsaturated and saturated fatty acids and/or salts thereof.

5. The emulsion composition according to claim 1 wherein the mean number of carbon atoms of the unsaturated fatty acids and/or salts thereof is at least 4 carbon atoms greater than the mean number of carbon atoms present in the saturated fatty acids and/or salts thereof.

6. An emulsion comprising:
   (i) an oil phase,
   (ii) at least one pest control active,
   (iii) a mixture of:
      a) unsaturated C12-C26 fatty acids and/or salts thereof; and
      b) saturated C6-C14 fatty acids and/or salts thereof, wherein greater than 70% by weight of the saturated fatty acids comprise 6 to 12 carbon atoms;
   (iv) an optional organic cosolvent, and
   (v) water;
   wherein the ratio of the unsaturated fatty acid component to the saturated fatty acid component in the emulsion is in the range from 0.2 to 5:1 by weight.

7. The emulsion according to claim 6 wherein the pest control active is a plant essential oil.

8. The emulsion according to claim 7 wherein the pest control active is thyme oil, geraniol, and/or wintergreen oil.

9. The emulsion according to claim 6 wherein the oil phase comprises a blend of isopropyl myristate, geraniol and/or thyme oil white.

10. The emulsion according to claim 6 wherein the oil phase comprises a blend of isopropyl myristate, wintergreen oil and/or thyme oil white and thyme oil red.

11. The emulsion according to claim 6 wherein the mean number of carbon atoms of the unsaturated fatty acids and/or salts thereof is at least 4 carbon atoms greater than the mean number of carbon atoms present in the saturated fatty acids and/or salts thereof.

12. The emulsion according to claim 6 wherein the unsaturated fatty acid is selected from the group consisting of oleic, ricinoleic, linoleic, linolenic acids and mixtures thereof.

13. The emulsion according to claim 6 wherein the saturated fatty acid is selected from the group consisting of caprylic, capric, 2-ethyl hexanoic, trimethylhexanoic, trimethylnonanoic, tetramethylhexanoic acids, and mixtures thereof.

14. The emulsion according to claim 6 wherein the unsaturated fatty acids comprise at least one unsubstituted fatty acid and at least one hydroxy fatty acid.

15. The emulsion according to claim 6 comprising 0 to 50% by weight of free fatty acids and 50 to 100% by weight of fatty acid salts, based on the total weight of fatty acids and salts.

16. The emulsion according to claim 6 having a pH of 6 to 9.

17. The emulsion according to claim 6 wherein greater than 70% by weight of the unsaturated fatty acids comprise 14 to 24 carbon atoms.

18. The emulsion according to claim 6 wherein the combined mono-unsaturated and di-unsaturated fatty acids and/or salts thereof is greater than 75% by weight, based on the total weight of unsaturated fatty acids and salts thereof in the composition.

19. The emulsion according to claim 6 in the form of a transparent microemulsion.

20. The emulsion according to claim 6 which is stable at 50° C. for at least one month.

21. The emulsion according to claim 6 which is formed at low temperature and/or at low shear.

22. A method of forming an end-use pest control product comprising forming the emulsion composition of claim 1, comprising:
   1) combining:
      i) 3-50 wt. % of an oil phase;
      ii) 0.5-40 wt. % of the at least one pest control active; and
      iii) 3-50 wt. % of the mixture of:
         a) unsaturated C12-C26 fatty acids and/or salts thereof; and
         b) saturated C6-C14 fatty acids and/or salts thereof, wherein greater than 70% by weight of the saturated fatty acids comprise 6 to 12 carbon atoms;
         wherein the ratio of the unsaturated fatty acid component to the saturated fatty acid component in the composition is in the range from 0.2 to 5:1 by weight;
      iv) optionally, 0-20 wt. % of an organic cosolvent; and
      v) water; and
   2) diluting said emulsion with water up to 15 times.

23. The method of claim 22, wherein said emulsion is diluted 1 to 7 times with water.

24. The method of claim 22, wherein 0-20 wt. % of an organic cosolvent is combined in said emulsion.

* * * * *